United States Patent
Daniel et al.

(10) Patent No.: US 10,437,958 B2
(45) Date of Patent: Oct. 8, 2019

(54) DEVICE AND METHOD FOR MONITORING THE TREATMENT OF A PATIENT

(71) Applicant: Fresenius Medical Care Deutschland GmbH, Bad Homburg (DE)

(72) Inventors: Pia Daniel, Bodman (DE); Marco Graefe, Bad Homburg (DE); Michael Luckau, Lohmar (DE); Helmut Steil, Gelnhausen (DE); Klaus Wolf, Muedesheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 347 days.

(21) Appl. No.: 14/075,201

(22) Filed: Nov. 8, 2013

(65) Prior Publication Data
US 2014/0129250 A1    May 8, 2014

Related U.S. Application Data

(60) Provisional application No. 61/723,978, filed on Nov. 8, 2012.

(30) Foreign Application Priority Data

Nov. 8, 2012   (DE) .................... 10 2012 021 805

(51) Int. Cl.
    *G06F 19/00*      (2018.01)
    *G16H 40/63*      (2018.01)

(52) U.S. Cl.
    CPC ......... *G06F 19/3418* (2013.01); *G16H 40/63* (2018.01)

(58) Field of Classification Search
    CPC .... G06Q 50/22; G06Q 50/24; G06F 19/3418; G16H 40/63

(Continued)

(56) References Cited

U.S. PATENT DOCUMENTS

| 5,555,891 A * | 9/1996 | Eisenfeld ............. A61B 5/0809 600/534 |
| 2003/0055606 A1 | 3/2003 | Christ et al. |

(Continued)

FOREIGN PATENT DOCUMENTS

| DE | 102008054442 | 6/2010 |
| EP | 1260173 | 11/2002 |

(Continued)

OTHER PUBLICATIONS

Otero, A., Palacios, F., Akinfiev, T., & Fernandez, R. ( ). A device for automatically measuring and supervising the critical care patient's urine output. Sensors (Basel, Switzerland), 10(1), 934-951. doi:10.3390/s100100934 (Year: 2010).*

(Continued)

*Primary Examiner* — Eliza A Lam
(74) *Attorney, Agent, or Firm* — Jacobson Holman, PLLC.

(57) ABSTRACT

A method for monitoring the treatment of a patient in his home environment is provided. The method includes supplying treatment-related data to a home treatment unit, transmitting the treatment-related data from the treatment, analyzing the treatment-related data with respect to an ideal state or a normal state or for the success of a treatment by the monitoring unit, detecting a deviation from an ideal state or a normal state, requesting additional treatment-related data from the home treatment site with respect to the deviation found, supplying the additional treatment-related data, and transmitting the additional treatment-related data to the monitoring unit.

13 Claims, 4 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 2010/0087770 A1 | 4/2010 | Bock et al. | |
| 2010/0137693 A1 | 6/2010 | Porras et al. | |
| 2011/0105979 A1 | 5/2011 | Schlaeper et al. | |
| 2011/0301429 A1 | 12/2011 | Henke | |
| 2012/0041771 A1* | 2/2012 | Cosentino | G06Q 50/22 |
| | | | 705/2 |

FOREIGN PATENT DOCUMENTS

| | | | |
|---|---|---|---|
| EP | 2656785 A1 * | 10/2013 | ........... A61B 5/0537 |
| JP | 2001346870 | 12/2001 | |
| JP | 2009034543 | 2/2009 | |

OTHER PUBLICATIONS

Görs et al. "Tele-Medicine Techniques for Remote Support of Patients in Dialysis and COPD." 2011 International Conference on Instrumentation, Communication, Information Technology and Biomedical Engineering, Nov. 8-9, 2011, pp. 23-28.

* cited by examiner

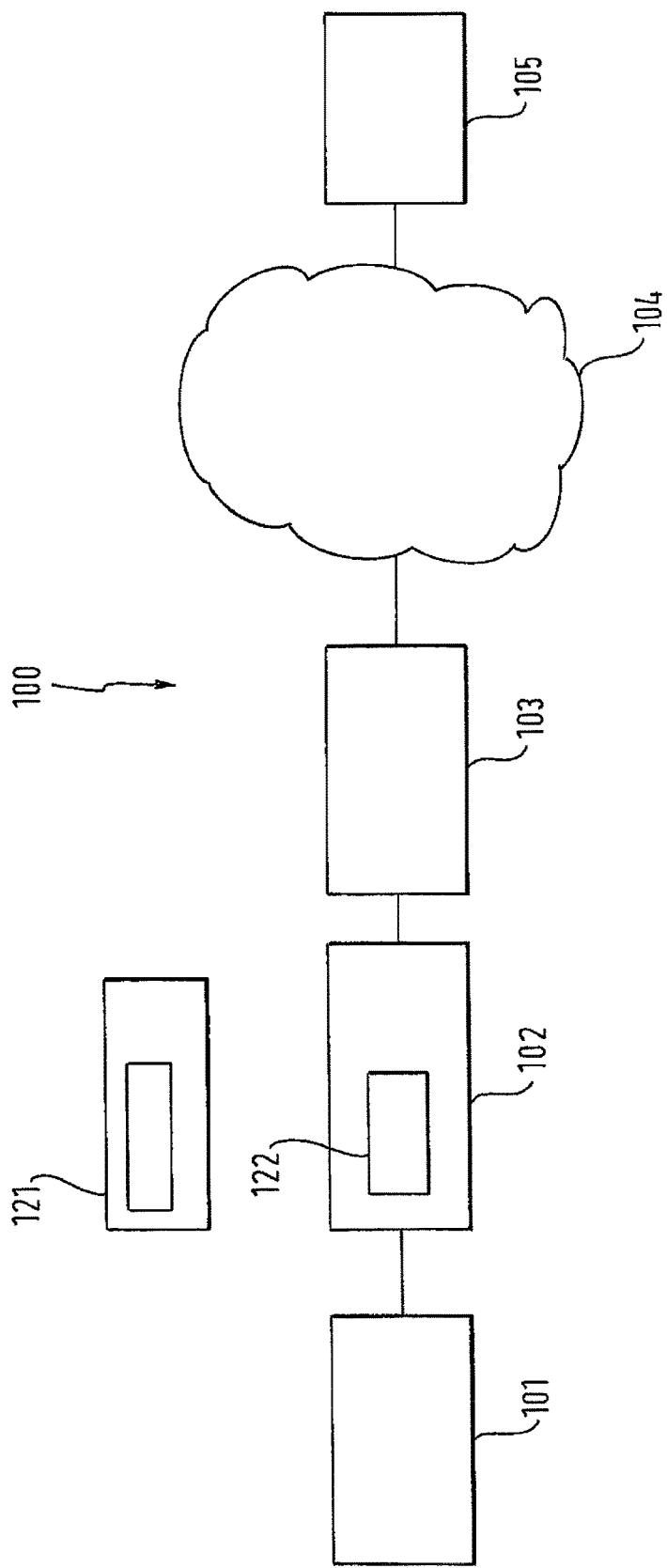

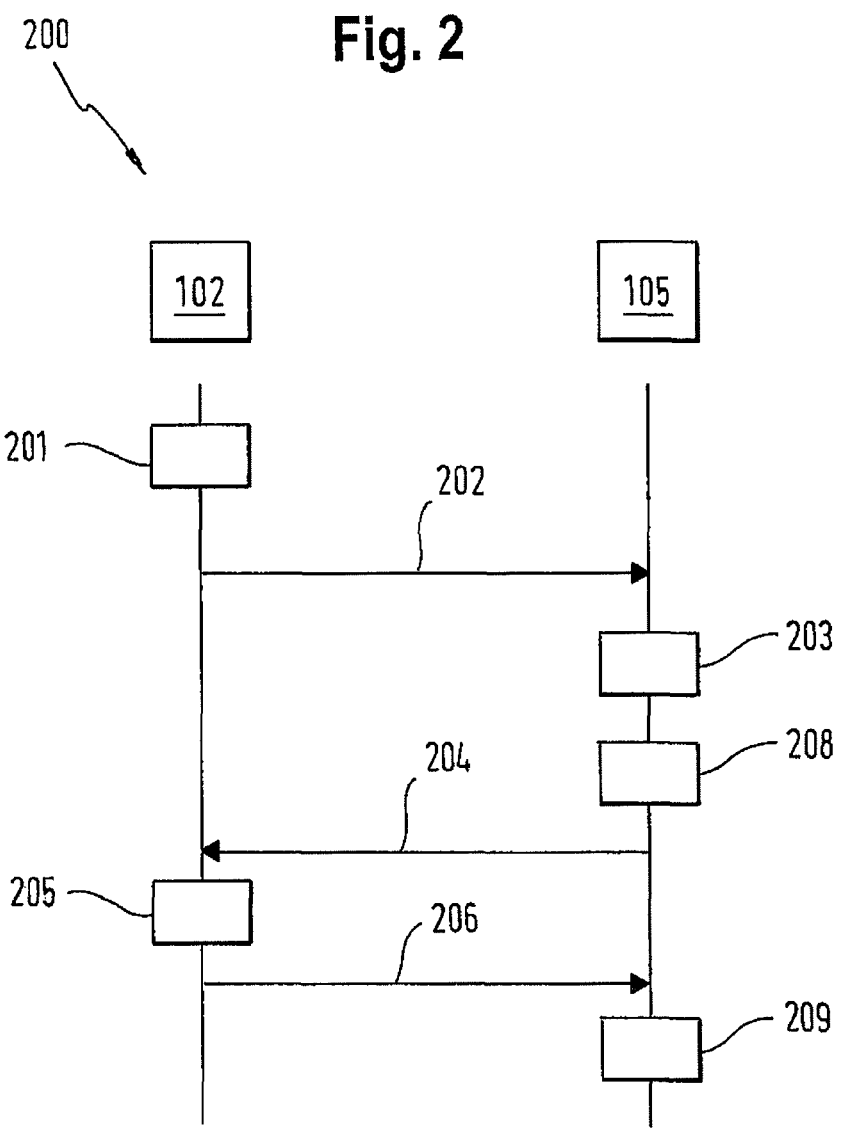

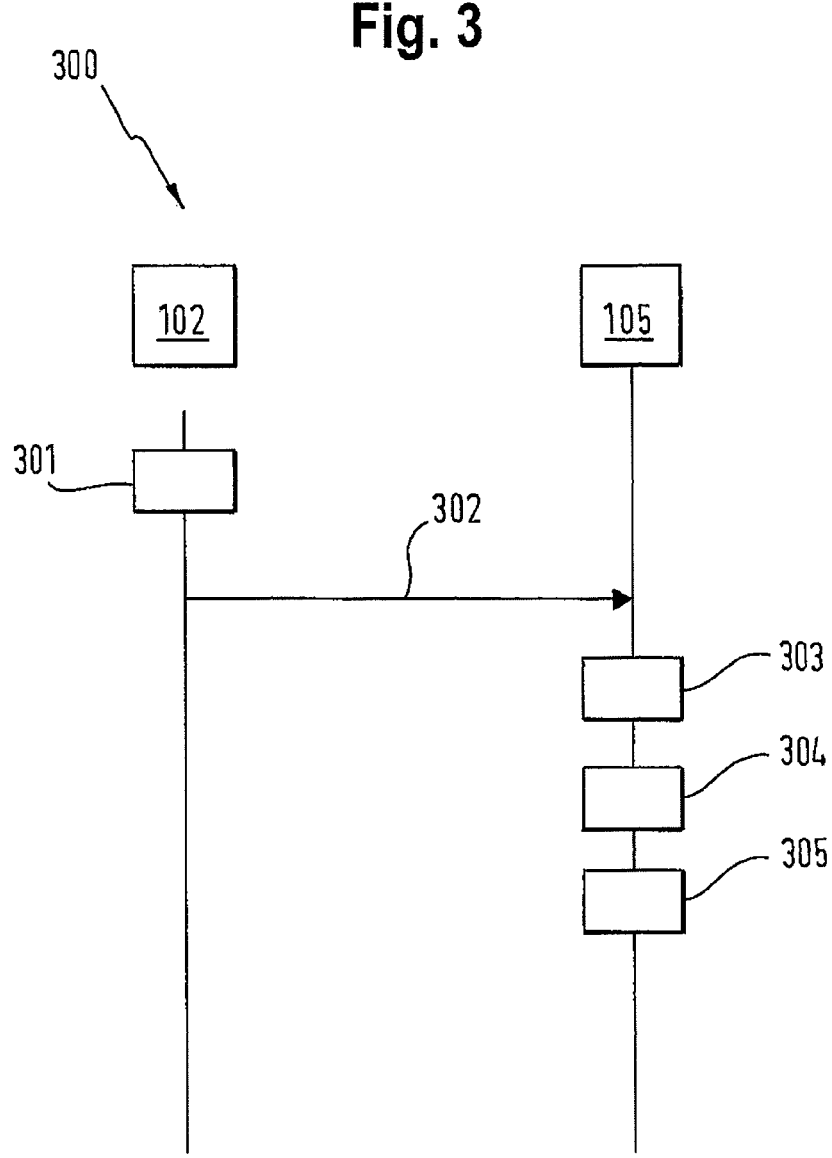

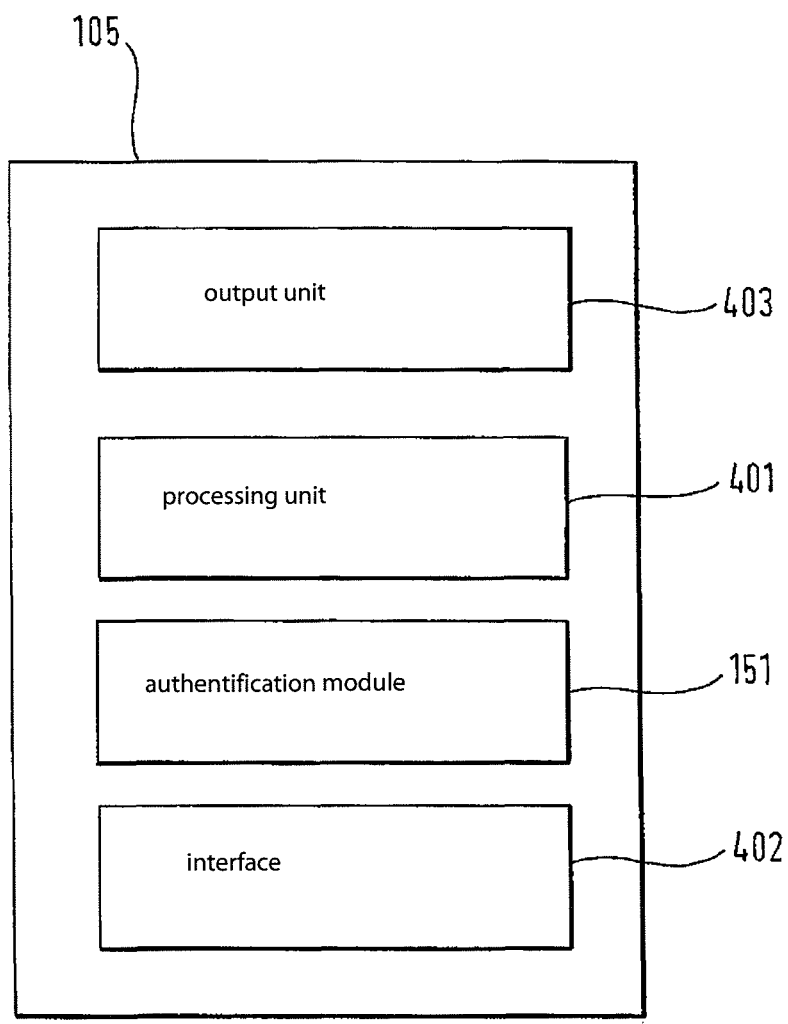

DEVICE AND METHOD FOR MONITORING THE TREATMENT OF A PATIENT

BACKGROUND OF THE INVENTION

1. Field of the Invention

The invention relates to the field of treatment of patients in their home environment.

2. Description of the Related Art

In addition to treatment of patients in medical offices, clinics or policlinics, treatment of patients in their home environment has gained a certain importance, especially in the care of chronically ill patients.

An example given here is care of patients in chronic renal failure by dialysis, in particular hemodialysis and peritoneal dialysis.

In hemodialysis, blood is withdrawn continuously from a patient in an extracorporeal circulation, passed through a hemodialyzer and reinfused back into the patient. In doing so, a mass exchange resembling that performed in the kidneys takes place. The hemodialyzer consists of two chambers separated by a semipermeable membrane, one chamber having blood flowing through it and the other chamber having a purifying fluid—the dialysis fluid—flowing through it. Commercial hemodialyzers usually have thousands of hollow fibers to perform this task, the walls of these fibers being semipermeable for the substances to be exchanged. Blood passes through the hollow fibers on the inside while the dialysis fluid is usually fed into the fiber interspace and removed in the opposite direction.

The dialysis fluid has concentrations of blood constituents such as electrolytes, which correspond approximately to those found in a healthy person, so that corresponding concentrations can be maintained at a normal level in the blood. Substances such as creatinine or urea to be removed from the blood are not present in the dialysis fluid, so these are removed from the blood by diffusion just because of the concentration gradient on the membrane. With the help of a pressure gradient, excess water is removed from the blood by convection and/or ultrafiltration.

Hemodialysis machines, which usually also ensure the preparation of the dialysis fluid from water and concentrates with the correct composition and temperature are used to control such processes. This liquid is also used in today's hemodiafiltration machines to balance a blood purification (hemofiltration) performed by increased convection. In hemodiafiltration, a larger quantity of ultrafiltrate is removed from the patient's blood during a hemodialysis treatment by the hemodialyzer and this amount is replaced with substitution fluid except for the total quantity of liquid to be removed. In modern machines for treatment of chronic renal failure, the dialysis fluid prepared online is used for this by the fact that a line which branches off from the dialysis fluid circulation is provided with one or more filter stages and connected to the extracorporeal blood circulation upstream and/or downstream from the hemodialyzer. The additional filtered dialysis fluid, which is added to the blood circulation, is referred to as dilution.

As an alternative to treatment of patients with hemodialysis machines at a dialysis center, treatment of patients in their home environment has a certain importance; this is so-called home hemodialysis. This can be performed by trained personnel, for example, a dialysis nurse or the patient himself or family members can be trained in performing the dialysis treatment.

Another popular type of dialysis treatment is peritoneal dialysis, in which an artificial access to the patient's abdominal cavity is created so that sterile pyrogen-free dialysis fluid can be infused into the abdominal cavity through this access. The peritoneal membrane functions as a natural dialyzer through which toxic uremic metabolites and various ions can pass from the patient's bloodstream into the dialysis fluid according to a concentration gradient. At the same time water enters the peritoneum because of the osmotic gradient. Dialysis fluid is removed in various cycles, discarded and replaced with these cycles following one another according to a predetermined scheme which is controlled by the patient or is performed automatically by the peritoneal dialysis machine. Peritoneal dialysis is very commonly performed in the home area, in which case it is known as home peritoneal dialysis.

In home hemodialysis and in home peritoneal dialysis, the patient presents at a dialysis center at regular intervals, for example, at intervals of 4-6 weeks. The object of the present invention is therefore to improve the monitoring of home patients in the times between visits at the corresponding centers.

SUMMARY

This object is achieved by a method for monitoring the treatment of a patient, in particular a home patient, including the steps of supplying treatment-related data to a home treatment unit, transmitting the treatment-related data from the treatment unit to a remote monitoring unit for monitoring the treatment, analyzing the treatment-related data with respect to an ideal state or a normal state or for the success of a treatment by the monitoring unit, ascertaining a deviation from an ideal state or a normal state, requesting additional treatment-related data from the home treatment site with respect to the deviation found, supplying the additional treatment-related data, and transmitting the additional treatment-related data to the monitoring unit.

The object may also be achieved by a method for monitoring the treatment of a patient, in particular a home patient, including supplying a plurality of a treatment-related data originating from a plurality of home treatment units, analyzing the plurality of treatment-related data with respect to a particular ideal state or normal state or the result of a treatment by the monitoring unit, assigning a priority with respect to the need for intervention and/or the need for checking on a treatment by a caregiver and/or a visual observation of a patient by the caregiver, and directing the attention of a caregiver to a certain patient as a function of the assigned priority.

In addition, the present object is achieved by a monitoring unit for monitoring a patient's treatment in his home environment, including an interface for receiving treatment-related data from a treatment unit, an output unit and a processing unit adapted for performing the first foregoing method. The present invention object is also achieved by a computer program product including program code parts adapted for performing the first foregoing method. Advantageous embodiments include 1) the step of ascertaining a deviation from an ideal state or a normal state which includes an allocation to a certain symptom cluster, where the request for additional treatment-related data is made as a function of the specific symptom cluster; 2) using a certain evaluation algorithm determined on the basis of the symptom cluster for the assignment of priority with respect to a need for intervention and/or a need for a check on a treatment by a caregiver and/or a visual observation of a patient by a caregiver; 3) using an expert system for analysis of the plurality of treatment-related data; 4) supplying the treatment-related data at a plurality of points in time where the analysis of the treatment-related data comprises a time series analysis; 5) the monitoring unit being part of a hospital information system in which authentication means are provided for authentication of a certain patient or a certain caregiver, and including the steps of using the treatment unit for input of authentication data by an authentication means for authenticating a patient or a caregiver in the hospital information system, and authenticating the patient on the basis of the input authentication data; 6) the treatment unit being a blood treatment machine, preferably a hemodialysis machine or a peritoneal dialysis machine; 7) the monitoring unit being part of a hospital information system, in which guidelines with ideal values for a hemodialysis treatment to be performed or a peritoneal dialysis treatment to be performed are stored as one or more data records, where the analysis of the treatment-related data is performed with regard to a deviation from the setpoint specifications of the guidelines; 8) the treatment-related data or the additional treatment-related data being selected from a list of: a dialysis dose, an ultrafiltration volume, bioimpedance data including a body composition and/or hyperhydration detected by means of bioimpedance data, a blood pressure, a patient's body temperature, image data on a catheter inlet/outlet site, and a patient's weight; 9) the analysis of the image data of a catheter inlet/outlet site including automatic image processing of the image data; and 10) the treatment-related data or the additional treatment-related data being traced back to user input at a user interface of the treatment unit and wherein the user input relates to the answers to questions to the patient.

BRIEF DESCRIPTION OF THE DRAWINGS

Additional details and advantages of the invention are described in greater detail on the basis of an exemplary embodiment as illustrated in the drawings.

FIG. 1 shows a block diagram of a monitoring system with a treatment unit and a monitoring unit.

FIG. 2 shows a flowchart of a first method for monitoring the treatment of a patient, in particular a home patient.

FIG. 3 shows a flowchart of another method for monitoring the treatment of a patient, in particular a home patient FIG. 4 shows a block diagram of a monitoring unit.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE DRAWINGS

FIG. 1 shows a monitoring system 100 for monitoring a patient in a home environment, in order words: that of a home patient is shown schematically. The monitoring system 100 has at least one treatment unit, or in a certain embodiment, a plurality of treatment units 102 for treatment of patients in their respective home environment or, in other words, home treatment units. For the sake of simplicity, FIG. 1 shows only one home treatment unit 102. An embodiment of a home treatment unit 102 is a home dialysis machine, e.g., a home hemodialysis machine or a home peritoneal dialysis machine.

The home treatment unit has a data source 101 for the treatment-related data or is connected to a data source 101 for treatment-related data.

Possible embodiments of a data source 101 for treatment-related data include a blood glucose meter, a sphygmomanometer, patient scales or a fluid management system or a system for determining a state of hyperhydration or hypohydration in a patient. The latter can be accomplished as a fluid balance for this treatment, for example, by compiling a balance of fluid administered and fluid withdrawn in a dialysis treatment, for example. Alternatively or additionally, a fluid status may be determined on the basis of a determination of the patient's body composition, for example, by means of bioimpedance measurement methods performed during the treatment. The Body Composition Monitor distributed by the present patent applicant is one example of such a system for determining the hyperhydration or hypohydration.

Another example of a data source 101 for treatment-related data is a data input device for manual input of measured data on the devices described here or, for example, a certain medication received by a patient or consumable materials used in the treatment, for example, a dialyzer used during a hemodialysis treatment. In the latter case, the data source may also be a barcode scanner for scanning in a corresponding barcode.

In the case of dialysis, additional data sources 102, which supply treatment-related data, relate to uses of the dialysis machine that is used, such as electric current or water usage or to the condition of the water used, for example, the status including an error status or a disinfection status of a reverse osmosis system.

The data source 101 may be integrated into the treatment unit 102 or may be separate from it. In the latter case, it may also be implemented by a traditional personal computer or by a traditional mobile telephone, smartphone or the like, inasmuch as a corresponding interface such as a Bluetooth interface is provided in the treatment unit. In the case of a peritoneal dialysis machine as the treatment unit, the data source may also be embodied as a camera for detecting a catheter outlet.

In addition, the treatment unit 102 has a connection via a home gateway 103 to a transmission network 104 and from there to a monitoring unit 105.

The transmission network 104 may comprise parts of the public Internet, wherein an interface to a closed clinic network into which the analysis unit 105 is integrated may be provided.

The monitoring unit 105 may be implemented on one computer or distributed among several computers.

The treatment unit 102 and the monitoring unit 105 together form a monitoring system 104 for monitoring a home patient.

The treatment unit 102 may comprise a data reader 122 or may be connected to the latter for input of identification data on a home patient from identification means such as a card reader for entering patient data from a patient card 121.

In order for a patient treated by the treatment unit 102 to be monitored by monitoring unit 105, methods for monitoring a home patient and, associated with that, an exchange of messages between the treatment unit 102 and the monitoring unit 105 are depicted in FIGS. 2 and 3.

In the method for monitoring the treatment of a patient 200 shown in FIG. 2, treatment-related data are supplied to the home monitoring unit in a step 201. This may take place within the context of ongoing monitoring of the treatment of the home patient, for example, as part of ongoing monitoring of a dialysis treatment.

At the start of a treatment, there is normally an identification procedure, in which the patient data from a patient identification means 121 are entered using the data reader unit 122 and are transmitted to the monitoring unit 105. The patient's identification may include authentication by an authentication unit 151, which is contained in or allocated to the monitoring unit.

Thus, as part of this ongoing monitoring of the treatment, reaching a certain dialysis does Kt/V or a certain ultrafiltrate quantity as a function of the treatment time or in conclusion of the treatment can be detected as treatment-related data. Additional embodiments of treatment-related data include data recorded at the start of or during the treatment representing a patient's body composition, for example, by using bioimpedance measurement methods. Other embodiments of treatment-related data include, for example, a patient's temperature or blood pressure or images of a catheter outlet, these images being recorded at the start of, during or after conclusion of a treatment.

In a transmission step 202, the treatment-related data are transmitted from the treatment unit 101 to a remote monitoring unit 105 for monitoring the treatment.

For treatment-related data, reference data representing an ideal or uncomplicated course of a treatment, an unremarkable condition of the home patient or a desired treatment result or whether the treatment conforms to treatment guidelines are made available. This may be accomplished, for example, by the monitoring unit 105. If the monitoring unit 105 is part of a clinic network or a hospital information system, treatment guidelines which would otherwise be used in treatment of clinic patients may thus be used for treatment of home patients. The reference data may be predetermined for the individual patient or may be valid for all patients uniformly. In the former case, the reference data may be selected on the basis of previously transmitted patient identification data.

The treatment-related data are analyzed in the monitoring unit 105 in an analysis step 203 with regard to an ideal state or a normal state or with regard to a treatment result in order to detect a possible deviation from the ideal state or the normal state or to ascertain whether or not a certain treatment result has occurred.

Analysis of the treatment-related data may comprise, for example, a time series analysis of the treatment-related data. For example, a reference profile may be created for a hemodialysis treatment, for example, an ultrafiltration profile or a reference profile for the urea clearance Kt/V to be achieved over the course of the treatment. In this case, the comparison of the treatment-related data with corresponding reference data may include a comparison at a corresponding reference point in time.

Other examples of reference data include reference values for the blood pressure, for the body temperature, the fat content, the water content or other reference values for the body composition.

In this case, a time series analysis may comprise a trend analysis in order to ascertain, for example, whether the change in blood pressure, body temperature or body composition is subject to a certain trend.

In a processing step 208 performed in the monitoring unit 105, the deviation from an ideal state or a normal state represented by one or more reference values is detected.

Information about a corresponding development in the condition of a home patient, for example, a developing sepsis, an increasing hyperhydration, a change detected in the body composition and the like, can be obtained in this way.

A deviation from an ideal or normal state may be detected by being assigned to a certain symptom cluster, for example, hyperhydration, sepsis, a certain blood pressure or the like.

As a response to a detected deviation in the treatment-related data from an ideal state or a normal state, the monitoring unit requests additional treatment-related data with a request message 204 to the home treatment unit 201. The additional treatment-related data may be selected as a function of the symptom cluster determined previously.

The request for additional treatment-related data may be made in such a way that the request message contains an indicator about which type of additional treatment-related data is being requested. The type of additional treatment-related data may be a function of the deviation and/or symptom cluster ascertained previously.

For example, if a rise in body temperature of a peritoneal dialysis patient is detected over a period of several treatments, the possibility of a developing sepsis must be recognized and a photograph of a catheter outlet site must be requested to corroborate this suspicion.

The connection of the treatment-related data originally transmitted and the additional treatment-related data is usually such that an initial suspicion based on analysis of the treatment-related data originally provided may or may not be supported by the additional treatment-related data.

Thus the data originally transmitted may include image data of a catheter outlet, said data being subjected to an automatic image analysis to ascertain characteristic shape parameters of the catheter outlet and to compare them with reference values. Based on the found deviation from a typical reference shape, a temperature measurement is then requested.

Another example is a trend in hyperhydration of a home patient detected on the basis of fluid balances; in support of this suspicion, a bioimpedance measurement is requested to ascertain a patient's body composition including the hydration status of the home patient.

The additional treatment-related data may also include answers to questions about the patient's condition selected on the basis of the type of deviation found in the patient.

Thus, a catalog of questions adapted to the symptom cluster of a hypertensive patient may be sent to the treatment unit 102 on the basis of a deviation found in the blood pressure of the home patient.

For additional symptom clusters, other catalogs of questions may also be supplied.

The additional treatment-related data are supplied in the treatment unit 102 in a recording step 205 followed by the transmission of the additional treatment-related data to the monitoring unit 105.

Supplying the treatment-related data may include the presentation of a catalog of questions to the home patient with the help of an input/output unit on the treatment unit 101 as well as the input of answers to the questions by the home patient. Alternatively or additionally, the home patient may also be instructed via the input/output device of the treatment unit 102 to perform additional measurements, such that the treatment-related data are then supplied using the data sources mentioned above.

The additional treatment-related data are then transmitted from the treatment unit 102 to the monitoring unit 105 in a transmission message 206.

An additional analysis 209 of the treatment-related data originally ascertained may then typically be performed in the monitoring unit in conjunction with the additional treatment-related data with the goal of confirming (or not) the deviation found from an ideal state or a normal state.

Joint analysis 209 of the treatment-related data transmitted originally and the additional treatment-related data may also be performed in such a manner that it is performed for a number of patients, such that there is a correlation of a value number or a priority and a priority is assigned with respect to a need for intervention and/or a need for a check on a treatment by a caregiver and/or a visual observation of a certain patient by a caregiver or the severity of the deviation found or of a symptom cluster is indicated.

The value number or priority may be allocated in such a way that an allocation made initially to a certain symptom cluster performed then triggers a corresponding evaluation algorithm according to which the joint analysis of the treatment-related data originally transmitted and the additional treatment-related data is to be performed.

Thus, for the symptom cluster of sepsis, an evaluation algorithm which determines the severity or the risk of sepsis may be determined on the basis of a joint analysis of image data of a catheter outlet and of temperature data and a corresponding value number or priority may be assigned.

For the symptom cluster of hyperhydration, another algorithm based on the analysis of fluid balances, weight measurements and/or a body composition may be selected.

FIG. 3 illustrates a method for monitoring a plurality of treatments of patient 300 in the patient's respective home environment, in which a number of home treatment units 101 regularly supply treatment-related data as shown in step 301 and transmit 302 the data to a central monitoring unit 105. Treatment-related data may thus be data obtained with the help of one of the data sources described in conjunction with FIG. 1. The treatment-related data include an identification of the respective patient being treated on a treatment unit 101. The method described in FIG. 3 may advantageously be performed in conjunction with the method described in FIG. 2.

In the central monitoring unit 105 the treatment-related data are analyzed in an analysis step 303 with regard to the respective ideal state or normal state or the success of a treatment, where the identification of the treated patient is assigned 304 a priority, which indicates the need for intervention and/or the need for a check on a treatment by a caregiver and/or a visual observation of a patient by a caregiver or the severity of a deviation found or a symptom cluster. In assigning a priority to a patient, additional criteria may also be taken into account, for example, the next scheduled examination appointment or the like.

In the next display step 305, a result of the step 304 is displayed to the caregiver on an output device of the monitoring unit 105 for the benefit of a treatment person in such a manner that the caregiver's attention is directed to a certain patient in accordance with the assigned priority.

For example, patient lists in which the patients are arranged in order of priority may be displayed and color codes may be issued and used to display the patient data or a different form of display may be selected, wherein it is advantageously ensured that the caregiver's attention is preferably directed to that patient for whom there is a need for intervention and/or a need for checking on the treatment by a caregiver and/or a visual observation of a patient by a caregiver or in whom there is a greater severity of a detected deviation or a symptom cluster.

FIG. 4 shows the structure of the monitoring unit 105 for monitoring the treatment of a patient. The monitoring unit 105 has an interface 402 for receiving treatment-related data in accordance with the methods described above in conjunction with FIGS. 2 and 3. In addition, the monitoring unit 105 has a processing unit 401 for processing the treatment-related data in accordance with one of the methods of FIGS. 2 and 3 and an output unit 403 for output of information for a caregiver as part of the method described in conjunction with FIG. 3. The monitoring unit 105 additionally advantageously has an authentication module 151 for performing a method for identification and/or authentication of a patient on the basis of data stored on patient identification means, for example, a patient card.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method of selectively transmitting data for monitoring the treatment of a patient undergoing dialysis via a catheter inlet/outlet site while in his home environment and for reducing a risk of sepsis, comprising:
   a home treatment unit that includes a blood treatment machine at a home treatment site receiving a first set of treatment-related data from at least one data source that includes a camera at the home treatment site;
   the blood treatment machine transmitting a second set of treatment-related data to a remote monitoring unit for monitoring the treatment, said second set of treatment-related data including the patient's body temperature;
   the monitoring unit analyzing the transmitted treatment-related data with respect to an ideal state or a normal state or for the success of a treatment;
   the monitoring unit detecting a deviation in the patient's body temperature from an ideal state or a normal state and, in response to detection of a rise in the body temperature over a period of several treatments, the monitoring unit requesting image data of the patient's catheter inlet/outlet site as additional treatment-related data from the home treatment site;
   the home treatment unit obtaining the additional treatment-related data including image data of the catheter inlet/outlet site from the camera;
   the home treatment unit transmitting the additional treatment-related data including the image data of the catheter inlet/outlet site to the monitoring unit as a third set of data, the monitoring unit performing an additional analysis of the treatment-related data and the additional treatment-related data; and
   if the rise in body temperature in conjunction with the image data of the catheter inlet/outlet site correspond with a symptom cluster consistent with a developing sepsis or risk thereof, the monitoring unit assigning the patient a priority for intervention based on the symptom cluster and a severity of the deviation as compared with other patients having their respective treatments monitored by the monitoring unit, the attention of a caregiver being directed to the patient according to the assigned priority and said caregiver checking on the treatment and/or visually observing the patient in accordance with the assigned priority in order to intervene to reduce the sepsis risk.

2. The method according to claim 1, further comprising an evaluation algorithm determined on the basis of the sepsis symptom cluster for the assignment of priority with respect to a need for intervention and/or a need for a check on a treatment by a caregiver and/or a visual observation of a patient by a caregiver.

3. The method according to claim 1, comprising using en expert system for analysis of the treatment-related data.

4. The method according to claim 1, wherein the treatment-related data are supplied at a plurality of points in time and wherein the analysis of the treatment-related data includes a time series analysis.

5. The method according to claim 1, wherein the monitoring unit is part of a hospital information system, in which authentication means are provided for authentication of a certain patient or a certain caregiver, comprising using the treatment unit for input of authentication data by an authentication means for authenticating a patient or a caregiver in the hospital information system, and authentication of the patient on the basis of the input authentication data.

6. The method according to claim 1, wherein the blood treatment machine of the treatment unit is a hemodialysis machine or a peritoneal dialysis machine.

7. The method according to claim 6, wherein the monitoring unit is part of a hospital information system, in which guidelines with ideal values for a hemodialysis treatment to be performed or a peritoneal dialysis treatment to be performed are stored as one or more data records, wherein the analysis of the treatment-related data is performed with regard to a deviation from the setpoint specifications of the guidelines.

8. The method according to claim 1, wherein the data source further includes user input at a user interface of the treatment unit and wherein the user input relates to the answers to questions asked of the patient.

9. A monitoring unit for transmitting and selectively receiving data for monitoring treatment of a plurality of patients including a patient undergoing dialysis via a catheter inlet/outlet site and for reducing a risk of sepsis while the patient is in his home environment, comprising:
an interface for receiving treatment-related data from a home treatment unit being used by the patient, an output unit and a processing unit adapted for performing a method including:
receiving, by the monitoring unit, treatment-related data transmitted from the home treatment unit, the home treatment unit including a camera, the treatment-related data including the patient's body temperature;
analyzing, by the monitoring unit, the received treatment-related data with respect to an ideal state or a normal state or for the success of a treatment;
detecting, by the monitoring unit, deviation in the patient's body temperature, from an ideal state or a normal state and, in response to detection of a rise in the body temperature over a period of several treatments, said monitoring unit requesting image data of the patient's catheter inlet/outlet site as additional treatment-related data from the home treatment site;
receiving, by the monitoring unit, additional treatment-related data including the image data of the patient's catheter inlet/outlet site as provided by the camera and transmitted from the home treatment unit, said monitoring unit performing an additional analysis of the treatment-related data and the additional treatment-related data; and
if the rise in body temperature in conjunction with the image data of the catheter inlet/outlet site correspond with a symptom cluster consistent with a developing sepsis or risk thereof, said monitoring unit assigning the patient a priority for intervention based on the symptom cluster and a severity of the deviation as compared with said plurality of patients having their respective treatments monitored by the monitoring unit, the attention of a caregiver being directed to the patient according to the assigned priority so that the caregiver can check on the treatment and/or visually observe the patient in accordance with the assigned priority in order to intervene to reduce the sepsis risk.

10. A non-transitory computer readable medium comprising computer program code parts executed on at least one computer and adapted for performing a method of selectively transmitting data for monitoring the treatment of a plurality of patients including a patient undergoing dialysis via a catheter inlet/outlet site while in his home environment for reducing a risk of sepsis, the method including:
receiving a first set of treatment-related data at a home treatment unit from at least one data source that includes a camera in communication with the home treatment unit;
transmitting a second set of treatment-related data from the treatment unit to a remote monitoring unit for monitoring the treatment, said second set of treatment-related data including the patient's body temperature;
analyzing, by the monitoring unit, the transmitted treatment-related data with respect to an ideal state or a normal state;
detecting a deviation in the patient's body temperature from an ideal state or a normal state and, in response to detection of a rise in the body temperature over a period of several treatments, the monitoring unit requesting image data of the patient's catheter inlet/outlet site as additional treatment-related data from the home treatment site;
obtaining the additional treatment-related data including image data of the catheter inlet/outlet side from the camera;
transmitting the additional treatment-related data including the image data of the catheter inlet/outlet site to the monitoring unit and performing an additional analysis of the treatment-related data and the additional treatment-related data; and
determining if the rise in body temperature in conjunction with the image data of the catheter inlet/outlet site correspond with a symptom cluster consistent with a developing sepsis or risk thereof;
upon determining correspondence exists with the symptom cluster, said monitoring unit assigning the patient a priority for intervention based on the symptom cluster and a severity of the deviation as compared with the plurality of patients having their respective treatments monitored by the monitoring unit, the attention of a caregiver being directed to the patient according to the assigned priority so that the caregiver can check on the treatment and/or visually observe the patient in accordance with the assigned priority in order to intervene to reduce the sepsis risk.

11. The method according to claim 1, wherein the treatment-related data further includes an ultrafiltration volume indicating a fluid balance and, if a trend in hyperhydration is detected on the basis of fluid balances, the method includes requesting a bioimpedance measurement as additional treatment-related data.

12. The non-transitory computer readable medium as set forth in claim 10, wherein said method performed by said at least one computer further comprises processing an ultrafiltration volume indicating a fluid balance and, if a trend in hyperhydration is detected on the basis of fluid balances, requesting a bioimpedance measurement as additional treatment-related data.

13. The monitoring unit as set forth in claim 9, wherein said processing unit is further configured to process an ultrafiltration volume indicating a fluid balance in connection with at least one of the plurality of patients being monitored and, if a trend in hyperhydration is detected on the basis of fluid balances, to request a bioimpedance measurement as additional treatment-related data in connection with said at least one of the plurality of patients.

\* \* \* \* \*